US012667341B2

(12) United States Patent
Bushman et al.

(10) Patent No.: US 12,667,341 B2
(45) Date of Patent: Jun. 30, 2026

(54) SYSTEM AND METHOD FOR URODYNAMIC ANALYSIS USING ULTRASOUND DATA

(71) Applicant: Wisconsin Alumni Research Foundation, Madison, WI (US)

(72) Inventors: Wade Bushman, Middletown, RI (US); Alejandro Roldán-Alzate, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 263 days.

(21) Appl. No.: 18/332,168

(22) Filed: Jun. 9, 2023

(65) Prior Publication Data

US 2024/0407763 A1 Dec. 12, 2024

(51) Int. Cl.
*A61B 8/00* (2006.01)

(52) U.S. Cl.
CPC .......... *A61B 8/5223* (2013.01); *A61B 8/5207* (2013.01)

(58) Field of Classification Search
CPC .................................................... A61B 8/5223
See application file for complete search history.

(56) References Cited

U.S. PATENT DOCUMENTS

2010/0204581 A1 * 8/2010 Chalana ............... A61B 8/4254
600/443

OTHER PUBLICATIONS

Hirahara et al., "Four-Dimensional Ultrasonography for Dynamic Bladder Shape Visualization and Analysis During Voiding", © 2006 by the American Institute of Ultrasound in Medicine • J Ultrasound Med 2006; 25:307-313.
Pewowaruk et al., "A pilot study of bladder voiding with real-time MRI and computational fluid dynamics", PLoS One 15(11): e0238404. Nov. 19, 2020, https://doi.org/10.1371/journal.pone.0238404.

* cited by examiner

*Primary Examiner* — Joseph M Santos Rodriguez
(74) *Attorney, Agent, or Firm* — Quarles & Brady LLP

(57) ABSTRACT

Methods and systems for ultrasound-based urodynamic evaluation are presented in the present disclosure. Pre-void and post-void ultrasound data of a bladder is acquired, in addition to a dynamic acquisition during voiding on a sagittal plane that encompasses the bladder, bladder neck and proximal urethra. The dynamic acquisition may be an ultrasound cine scan or a uroflowmetry measurement during voiding. Using semiautomatic segmentation, the volumes are quantified and virtual models are generated. Similarly, the ultrasound cine sagittal images are segmented to determine the deformation pattern of the bladder during voiding. Using an algorithm, a volume interpolation between pre and post void volumes is performed using the deformation profile obtained from the dynamic sagittal images as a constraint. Resolved bladder volumes are then analyzed using a computational fluid dynamics algorithm to derive flow rates and pressures and to calculate indices of contractility (BCI) and bladder obstruction (BOOI).

26 Claims, 9 Drawing Sheets

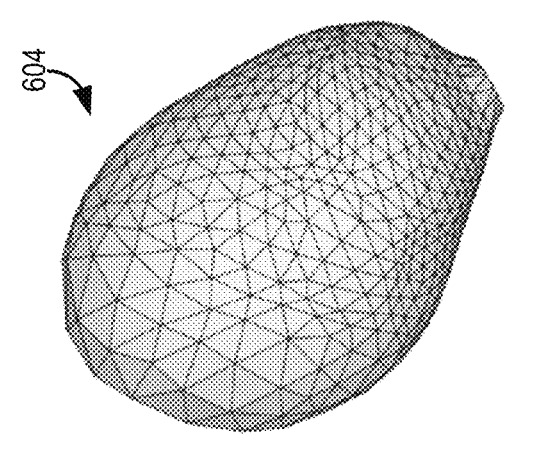

604

Mapped surface at $t = t_{i+1}$

FIG. 6C

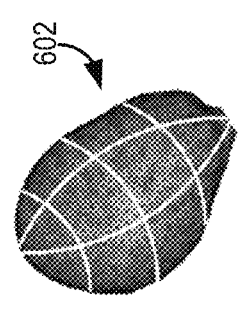

602

1. Calculate transformation matrix $A$ that maps $(\bar{z}_i, \bar{\theta}_i)$ to $(\bar{z}_{i+1}, \bar{\theta}_{i+1})$ 2. Partition surface at $t = t_{i+1}$ in longitudinal and angular directions 3. At each partition, search neighborhood of triangles closest to each triangle in surface at $t = t_i$ 4. Solve for radial distance required to intersect surface at $t = t_i$ with surface at $t = t_{i+1}$ using matrix $A$ 5. Repeat steps 1-4 for all partitions

FIG. 6B

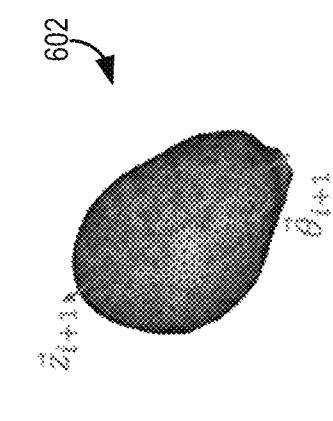

600

$\bar{z}_i$ $\bar{\theta}_i$

Surface at $t = t_i$ (mapped from surface $t = t_{i-1}$)

602

$\bar{z}_{i+1}$ $\bar{\theta}_{i+1}$

Unmapped surface at $t = t_{i+1}$

FIG. 6A

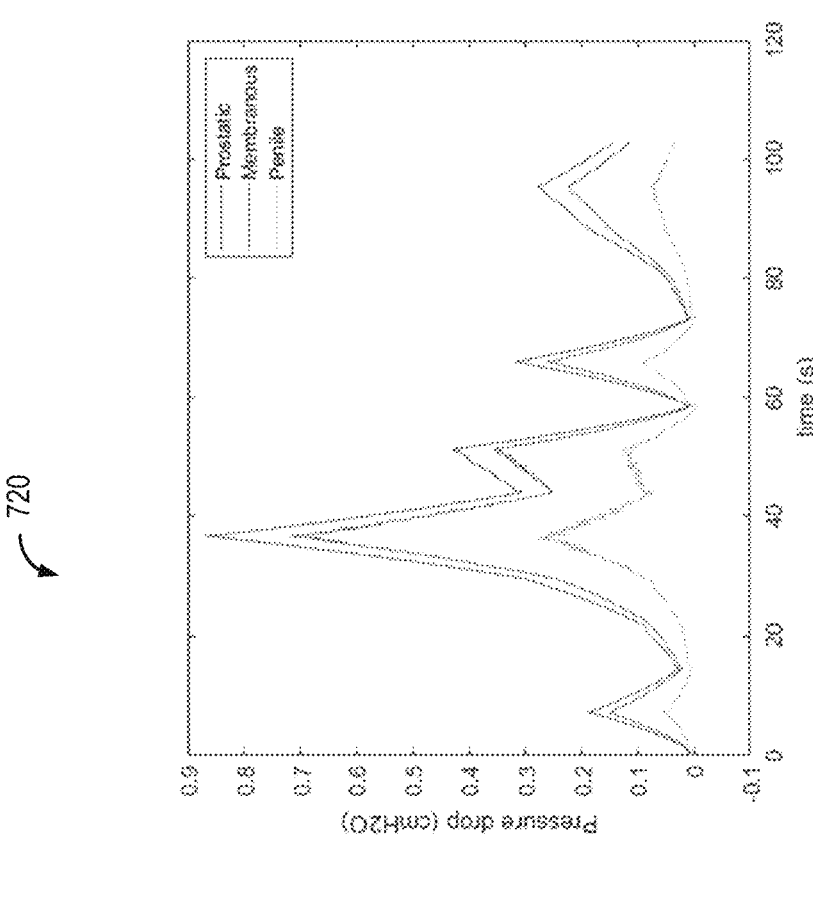
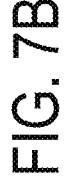
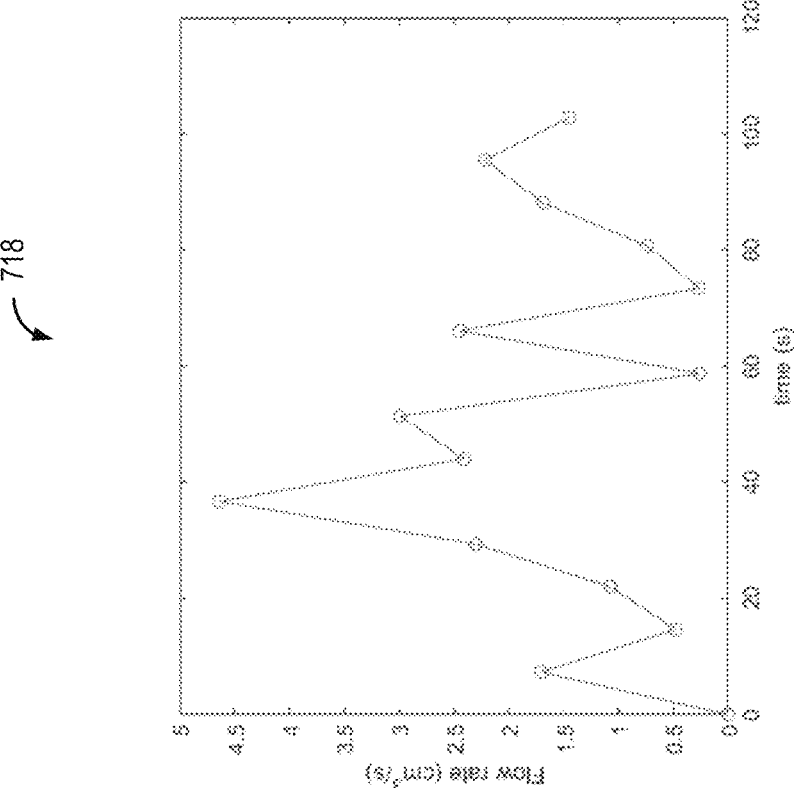
FIG. 7B

SYSTEM AND METHOD FOR URODYNAMIC ANALYSIS USING ULTRASOUND DATA

STATEMENT OF GOVERNMENT SUPPORT

This invention was made with government support under DK126850 awarded by the National Institutes of Health. The U.S. government has certain rights in the invention.

BACKGROUND

Lower urinary track symptoms (LUTS) and changes in bladder function occur frequently as individuals age. Studies have evaluated the anatomical and functional changes of the bladder in patients with LUTS; however, the biomechanical characteristics of the lower urogenital tract, and how these are altered in patients with LUTS, are not fully understood. Lower urinary tract function is commonly assessed through multi-channel urodynamic studies that determine bladder pressure and flow during voiding. These studies can be performed in combination with fluoroscopic imaging to visualize the urine flow during voiding. However, these studies are invasive and provide little insight into the changes in bladder anatomy and detrusor muscle function that occur with aging and lower urinary tract obstruction and other pathological conditions, such as diabetes. Further, such methods introduce ionizing radiation to the patient, which has known, undesirable health implications.

Thus, there is a continuing need for new methods that empower clinicians to better evaluate and understand conditions related to the urinary tract and, in particular, LUTS.

SUMMARY

The present disclosure addresses the aforementioned drawbacks by providing systems and methods that can utilize ultrasound to study urodynamics. For example, in one method, an ultrasound system may be used to acquire a pre-void (full bladder volume) ultrasound data, a subsequent dynamic acquisition during voiding, followed by post void (empty bladder volume) ultrasound data. The dynamic acquisition may be either an ultrasound cine scan or uroflowmetry measurement.

In accordance with one aspect of the present disclosure, using semiautomatic segmentation tools, the volumes are quantified, and virtual models are generated. Similarly, the dynamic (cine) sagittal images may be segmented to determine the deformation pattern of the bladder during voiding. Using an analogous algorithm, a volume interpolation between pre and post void volumes is performed using the deformation profile obtained from the dynamic sagittal images as a constraint. Resolved bladder volumes are then analyzed using a computational fluid dynamics algorithm to derive flow rates and pressures which then allow as to calculate indices of contractility (BCI) and bladder obstruction (BOOI).

In one aspect of the present disclosure, a method for urodynamic evaluation during voiding of a bladder is described. The method comprises receiving an ultrasound cine scan of a voiding event of a bladder of a subject, wherein the ultrasound cine scan includes images of a first bladder volume before the voiding event, of a second bladder volume after the voiding event, and of the voiding event between the first bladder volume and second bladder volume. The method further includes segmenting the image of the first bladder volume and the image of the second bladder volume to determine the first bladder volume and the second bladder volume, followed by generating a three-dimensional (3D) virtual model of the bladder from each of the first bladder volume and the second bladder volume. Additionally, the method includes deriving flow information during the voiding event and generating a flow curve from the flow information. Further, the method includes inputting the 3D virtual model and the flow curve into a computational fluid dynamics (CFD) model and generating a report using the inputs of the CFD model.

In one aspect of the present disclosure, an ultrasound imaging system is described. The system includes a transducer configured to transmit an ultrasound signal to a region of interest including a bladder of a subject during a voiding event and receive a reflected ultrasound signal from the region of interest. The system further includes a processor coupled to the transducer and configured to receive the reflected ultrasound signal and generate a plurality of images from the received signal of the region of interest during the voiding event. Further, the processor is configured to segment a first image of the region of interest to determine a first bladder volume and a second image of the region of interest to determine a second bladder volume. The processor is further configured generate a three-dimensional (3D) virtual model of the bladder from each of the first bladder volume and the second bladder volume. Additionally, the processor is configured to derive flow information during the voiding event and generate a flow curve from the flow information. The processor is further configured to input the 3D virtual model and the flow curve into a computational fluid dynamics (CFD) model and generate a report using the inputs of the CFD model.

In one aspect of the present disclosure, a method for urodynamic evaluation during voiding of a bladder is described. The method comprises acquiring imaging data from the patient while the patient is in one of an upright or seated position and the bladder is voided. Further the method includes determining, from the imaging data, a deformation of the bladder that occurred as the bladder is voided and pressure of the bladder as the bladder is voided and determining a flow curve of urine that occurred as the bladder is voided using a computational flow dynamics (CFD) model. The method further comprises generating a report describing function of the urinary tract as the bladder is voided using the deformation of the bladder, the pressure of the bladder, and the flow curve of the urine and displaying the report for clinical analysis of the function of the urinary tract.

These aspects are nonlimiting. Other aspects and features of the systems and methods described herein will be provided below

BRIEF DESCRIPTION OF THE DRAWINGS

The foregoing features of embodiments will be more readily understood by reference to the following detailed description, taken with reference to the accompanying drawings, in which:

FIG. 6A is a set of adjacent images being mapped in accordance with the present disclosure.

FIG. 6B shows a subsequent one of the adjacent images of FIG. 6A being partitioned and processed.

FIG. 6C shows a mapped surface carrying out the process described with respect to FIGS. 6A and 6B.

FIG. 7B shows plots of non-limiting examples of metrics that can be included in a report generated in accordance with the present disclosure.

DETAILED DESCRIPTION

Figure 1A:
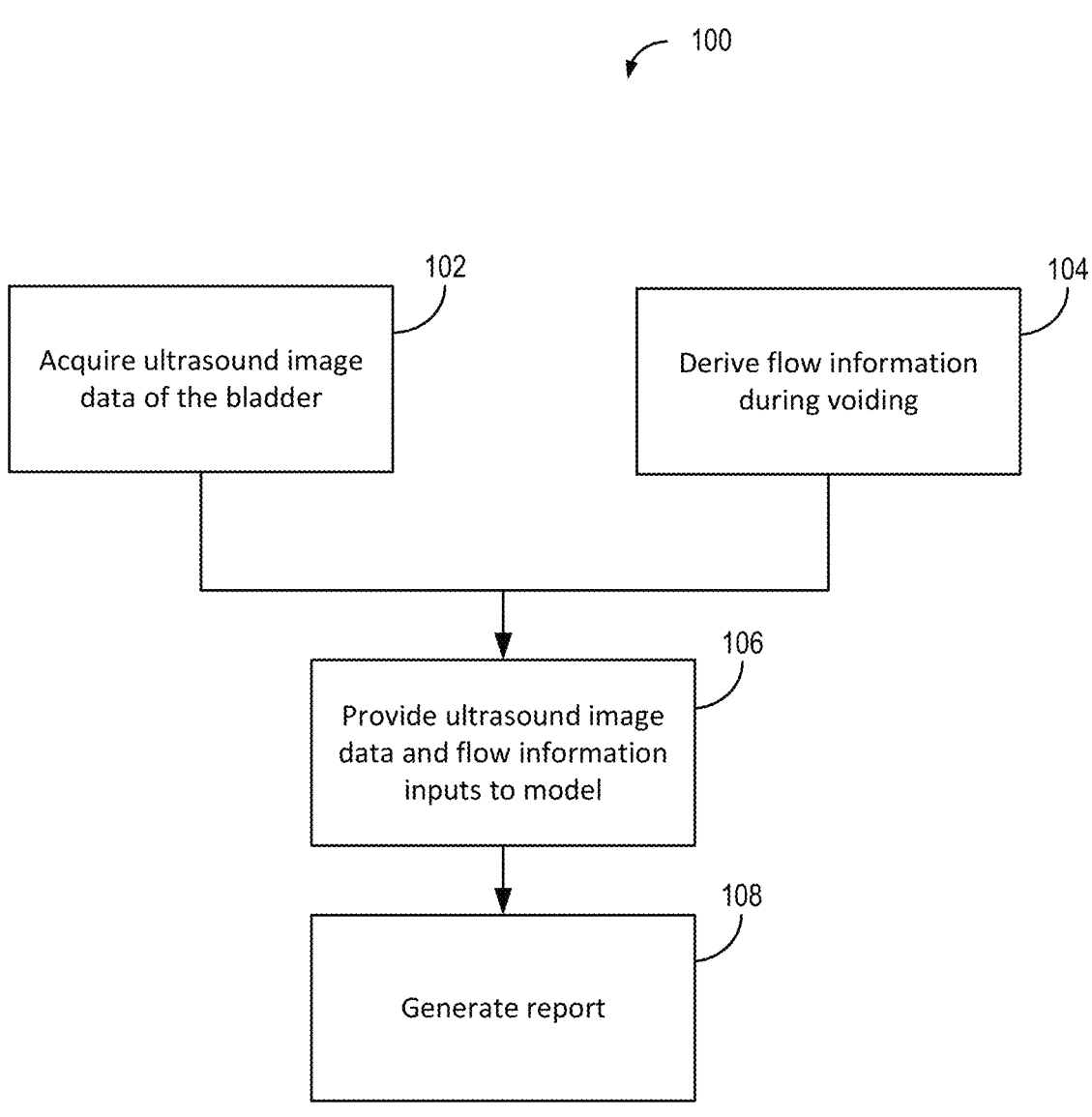
FIG. 1A is a flow chart setting forth general and non-limiting examples of steps of a process in accordance with the present disclosure.

The present disclosure provides systems and methods for urodynamic evaluation that utilize ultrasound images and/or uroflowmetry measurements, to calculate the pressure and flow during voiding without interpolation using CFD models. Measurements of bladder pressure and flow are normally made in clinical practice by multichannel urodynamics, using a small pressure-sensing catheter placed within the bladder and physical measurement of urine flow. The systems and methods provided herein are able to determine bladder pressure and flow measurements in a noninvasive fashion. A urine flow curve for the entire voiding effort can be created without relying on guessing or interpolating. Thus, maximum urine flow rate and the bladder pressure at maximum flow can be determined based on actual data and, thereby, consistent with the data-driven derivation of these metrics in multichannel urodynamics studies. That is, the present disclosure provides systems and methods to obtain the two metrics (normally obtained from multichannel urodynamics) that are central in the evaluation and treatment of patients with lower urinary tract symptoms—the bladder contractility index (BCI) and bladder outlet obstruction index (BOOI).

As used in this specification and the claims, the singular forms "a," "an," and "the" include plural forms unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover, the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or "B" or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

Referring to FIG. 1, a flow chart is provided that sets forth a general example of a method 100 in accordance with the present disclosure. In one configuration, at step 102, the process begins with the acquisition of ultrasound image data of the bladder such as using an ultrasound system as will be described below in FIGS. 2-4. The ultrasound data may be acquired over a period of time or may be acquired at discrete times. For example, the ultrasound data may be acquired while a full bladder and then a voided bladder. In a non-limiting example, the ultrasound image data may include an ultrasound cine scan of the bladder of a voiding event. In a non-limiting example, the ultrasound data is two-dimensional (2D) or three-dimensional (3D) imaging data. If acquired over the process of voiding, the ultrasound data may be acquired while the subject is in a standing or seated position, which is more comfortable for most subject to perform a bladder voiding. In another non-limiting example ultrasound image data is acquired of the bladder at a first bladder volume and a second bladder volume. In a non-limiting example, the first bladder volume may be the volume before the bladder is voided (full) and the second bladder volume is the volume at the end of voiding (empty). In one aspect, the first bladder volume is greater than the second bladder volume. In another aspect, the first bladder volume at a maximum bladder volume and the second bladder volume is at a minimum bladder volume.

At step 104, flow information is derived during a voiding process. In a non-limiting example, the flow information is derived from a plurality of images of the ultrasound cine scan during the voiding event. For example, the plurality of images of the voiding event includes images acquired between the first bladder volume and the second bladder volume.

However, as will be described, the flow information may also be derived from non-imaging data or a combination of imaging and non-imaging data. For example, non-imaging data may include uroflowmetry data or measurements, which can also be used to generate a flow curve. Uroflowmetry is a non-invasive diagnostic procedure that measures the volume of urine released (excreted) from the body, the speed with which the urine is excreted, and the duration of the excretion. In a non-limiting example, the information obtained in uroflowmetry tests can be used to evaluate the function of the lower urinary tract and/or it may help determining whether normal urine flow is obstructed.

For example, a system is used for measuring the urine voiding volume, urine voiding speed, and a total urine voiding time. These measurements may be used to generate a flow curve of the voiding event and inputted into the flow model described above. In a non-limiting example, the uroflowmetry may be a traditional system wherein the person urinates in a urine container and the speed measurements are preformed using any one of, but not limited to, a rotating disk method, capacitance-type cells, or weight-based load cells.

For example, using a weight-based load cell uroflowmetry system, urine is collected in a container having a predetermined diameter, and a load-cell serving as a sensor to measure the weight of the urine is provided under the container, thereby measuring the variation in the weight in the urination process. This measurement may be transmitted to urodynamic evaluation system according to aspects of the present disclosure.

Referring again to FIG. 1A, at step 106, the ultrasound image data and flow information are provided as inputs to a flow dynamics model. A report based on the inputs is generated at step 108, and may provide information related to bladder health. One particular and non-limiting example of the method 100 is provided in more detail below with reference to FIG. 1B.

Figure 1B:
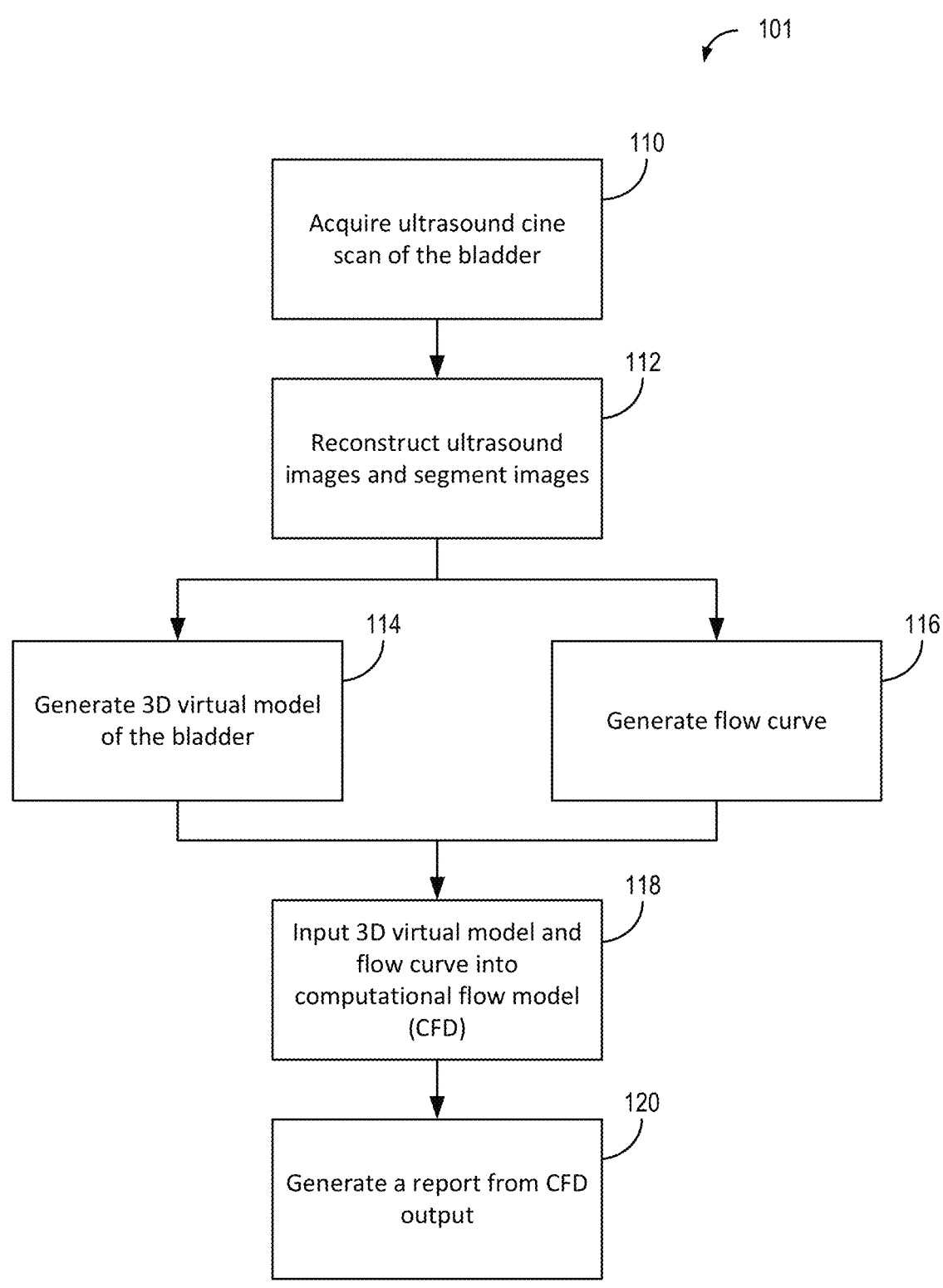
FIG. 1B is an example flow chart setting forth non-limiting examples of steps of a process in accordance with the present disclosure.

Referring now to FIG. 1B, a detailed non-limiting example process 101 begins at step 110 by performing an ultrasound cine scan of a bladder during a voiding event. In a non-limiting example, the ultrasound cine scan may be 2D ultrasound data. A cine scan based on bladder ultrasound data includes a plurality of sagittal ultrasound images acquired for a voiding event, including at a first bladder volume before voiding, at a second bladder volume after voiding, and during voiding between the first bladder volume and second bladder volume. In a non-limiting example, the ultrasound cine scan data is reconstructed into ultrasound images and segmented at step 112 to determine the first bladder volume, second bladder volume, and the relative displacement of the bladder wall during voiding. In a non-limiting example at step 114, 3D virtual models are generated of the first bladder volume before voiding and second bladder volume after voiding.

At step 116, a flow curve is generated from the images of the ultrasound cine scan acquired during voiding between the first bladder volume and second bladder volume. While acquiring images throughout the voiding process, specific points in time may be isolated determine bladder size and volume between each successive ultrasound image. From 2D ultrasound cine data acquired during voiding, the area of a sagittal plane through the bladder can be measured over time to generate a flow curve at step 116.

In a non-limiting example, to generate the 3D virtual models and estimate the motion of the bladder wall during voiding, for example, a spherical coordinate system can be defined for the bladder. The coordinate system origin can be set to be the center of the post voiding bladder volume. In general, the bladder wall displacement (d) is a three-dimensional vector that has spatial and time dependence given by, for example:

$$[d_r, d_\theta, d_\phi] = f(\theta, \phi, t) \qquad \text{Eqn. 1}$$

The complete description of bladder wall motion can be simplified by assuming the bladder wall only moves radially ($d_\theta = d_\phi = 0$) and the spatial and time dependence of the wall motion can be separated as:

$$d_r = d_0(\theta, \phi)\alpha(t) \qquad \text{Eqn. 2}$$

where $d_0(\theta, \phi)$ is the total displacement from the pre to post-void anatomies and $\alpha(t)$ is the time dependence function that varies from 0 at the start of voiding to 1 at the end of voiding. For wall displacement analysis, the bladder wall can be divided, for example, into anterior-posterior, dome-base, and left-right regions and an asymmetry ratio was calculated based on the difference between the median displacement of the left and right bladder wall regions. For each point on the bladder surface, $d_0$, the distance between the pre- and post-voiding anatomies can be calculated, for example, using a fast, minimum storage ray-triangle intersection algorithm. The time dependence function, $\alpha(t)$, can be calculated, for example, from real time measurements of bladder area during voiding, given by, for example:

$$\alpha(t) = \left( \frac{A(t) - A(t_0)}{A(t_{end}) - A(t_0)} \right)^{\frac{1}{2}} \qquad \text{Eqn. 3}$$

where $A(t)$ is the bladder area, to is the time at the start of voiding, and tend is the time at the end of voiding. Bladder area measurements from the real-time sagittal ultrasound cine images showed a sigmoidal behavior. Based on that behavior, $\alpha(t)$ can be chosen to be a square root of cosine function, for example.

Using these mathematical and computational methods, a pattern and symmetry of bladder contraction can be determined and used to predict patters of urine flow and vortices within the bladder using modeling. At step 118, the virtual models of the pre-void bladder and post void bladder from step 114 and the flow curve from the deformation of the bladder wall at step 116 are input and analyzed by a computational fluid dynamics (CFD) model. For example, patient-specific bladder anatomies can be imported into the CFD software. One example of CFD software is CON-VERGE v2.4 available from Convergent Science Inc, Madison, WI. Bladder wall motion can be estimated as described above and imposed with a user-defined function to virtually drive voiding. The urethra wall can be assumed to be rigid and the urethra outlet was set to atmospheric pressure. Vorticity, the curl of the velocity field, can be averaged over the bladder volume (urethra not included). Dimensionless vorticity can then be calculated based on average urethra flow rates and the prostatic urethra diameter for each subject.

At step 120, a report is generated from the CFD is output. For example, some non-limiting examples of metrics that are generated at step 120 can include velocity, pressure, wall shear stress, and vorticity. These metrics can be directly derived from the pre-voiding image, voiding images, and post-voiding image over the whole voiding process, rather than extrapolated or estimated, for example, for only a pre-void image and a post-void image. That is, regardless of the particular metrics, it is noted that the metrics produced are not interpolated or estimated from static or 2D images but can be derived directly from time-series volumetric images. As such, these metrics can be used to calculate useful indices used by urologists in clinical workflows, such as bladder outlet obstruction index (BOOI) and bladder contractility index (BCI). That is, because the metrics produced as described above are calculated directly from the cine data acquired over the dynamic process, metrics such as max flow and velocity at max flow can be determined with the accuracy and precision expected for use in clinical indices, such as BOOI and BCI, which have historically only been determined using max flow and velocity determined directly and invasively using multi-channel urodynamic studies.

Thus, a variety of metrics can be determined both at a given instance at over the entire voiding process, such as, for example, bladder capacity, voiding pressure, flow dynamics, pressure at maximum flow, post voiding residual volume, emptying efficiency, and maximum flow. Furthermore, these metrics can be readily used to calculate any of a variety of indices used in clinical decision making, such as BOOI and BCI. Additionally, the outputs of the CFD models may be used to create visualizations mapped to the volumetric movies created from the ultrasound data. Such visualizations can also be provided as part of the reports generated at step 120.

Figure 2:
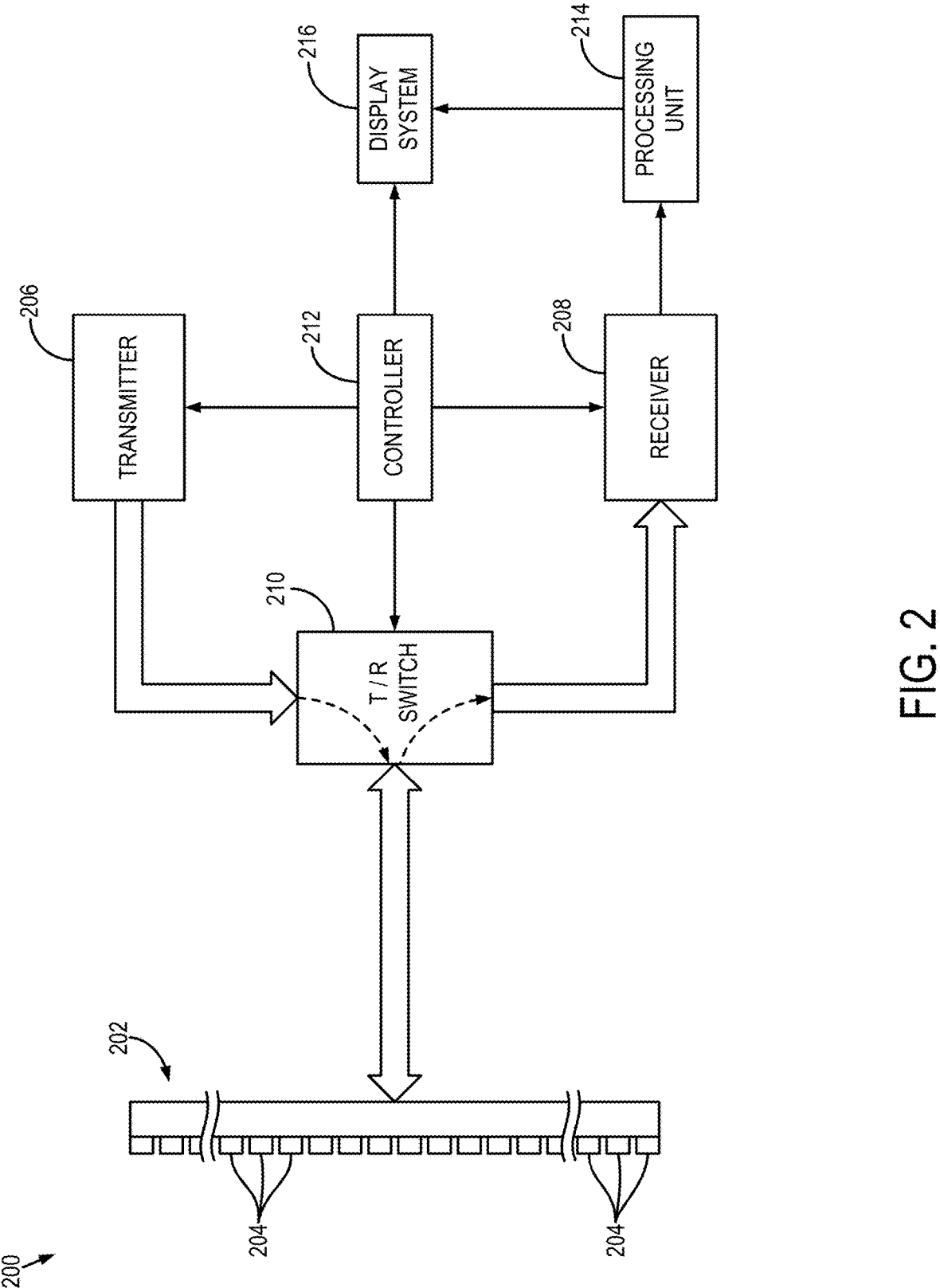
FIG. 2 is a block diagram of an example ultrasound system that can implement the methods described in the present disclosure.

FIG. 2 illustrates an example of an ultrasound system 200 that can implement the methods described in the present disclosure. The ultrasound system 200 includes a transducer array 202 that includes a plurality of separately driven transducer elements 204. The transducer array 202 can include any suitable ultrasound transducer array, including linear arrays, curved arrays, phased arrays, and so on. Similarly, the transducer array 202 can include a 1D transducer, a 1.5D transducer, a 1.75D transducer, a 2D transducer, a 3D transducer, and so on.

When energized by a transmitter 206, a given transducer element 204 produces a burst of ultrasonic energy, The ultrasonic energy reflected back to the transducer array 202 (e.g., an echo) from the object or subject under study is converted to an electrical signal (e.g., an echo signal) by each transducer element 204 and can be applied separately to a receiver 208 through a set of switches 210. The transmitter 206, receiver 208, and switches 210 are operated under the control of a controller 212, which may include one or more processors. As one example, the controller 212 can include a computer system.

The transmitter 206 can be programmed to transmit unfocused or focused ultrasound waves. In some configurations, the transmitter 206 can also be programmed to transmit diverged waves, spherical waves, cylindrical waves, plane waves, or combinations thereof. Furthermore, the transmitter 206 can be programmed to transmit spatially or temporally encoded pulses. The receiver 208 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 206 and the receiver 208 can be programmed to implement a high frame rate. For instance, a frame rate associated with an acquisition pulse repetition frequency ("PRF") of at least 100 can be implemented. In some configurations, the ultrasound system 200 can sample and store at least one hundred ensembles of echo signals in the temporal direction.

A scan can be performed by setting the switches 210 to their transmit position, thereby directing the transmitter 206 to be turned on momentarily to energize transducer elements 204 during one or more transmission events according to a selected imaging sequence. The switches 210 can then be set to their receive position and the subsequent echo signals produced by the transducer elements 204 in response to one or more detected echoes are measured and applied to the receiver 208, The separate echo signals from the transducer elements 204 can be combined in the receiver 208 to produce a single echo signal.

The echo signals are communicated to a processing unit 214, which may be implemented by a hardware processor and memory, to process echo signals or images generated from echo signals. As an example, the processing unit 214 can generate hemodynamic response data, functional maps, or other parametric maps using the methods described in the present disclosure. In some implementations, the processing unit 214 can also calculate or otherwise estimate optimized stimulation parameters, as described above. Additionally or alternatively, the processing unit 214 can output data to another computer system where these operations can be performed. Images produced from the echo signals by the processing unit 214 can be displayed on a display system 216.

Figure 3:
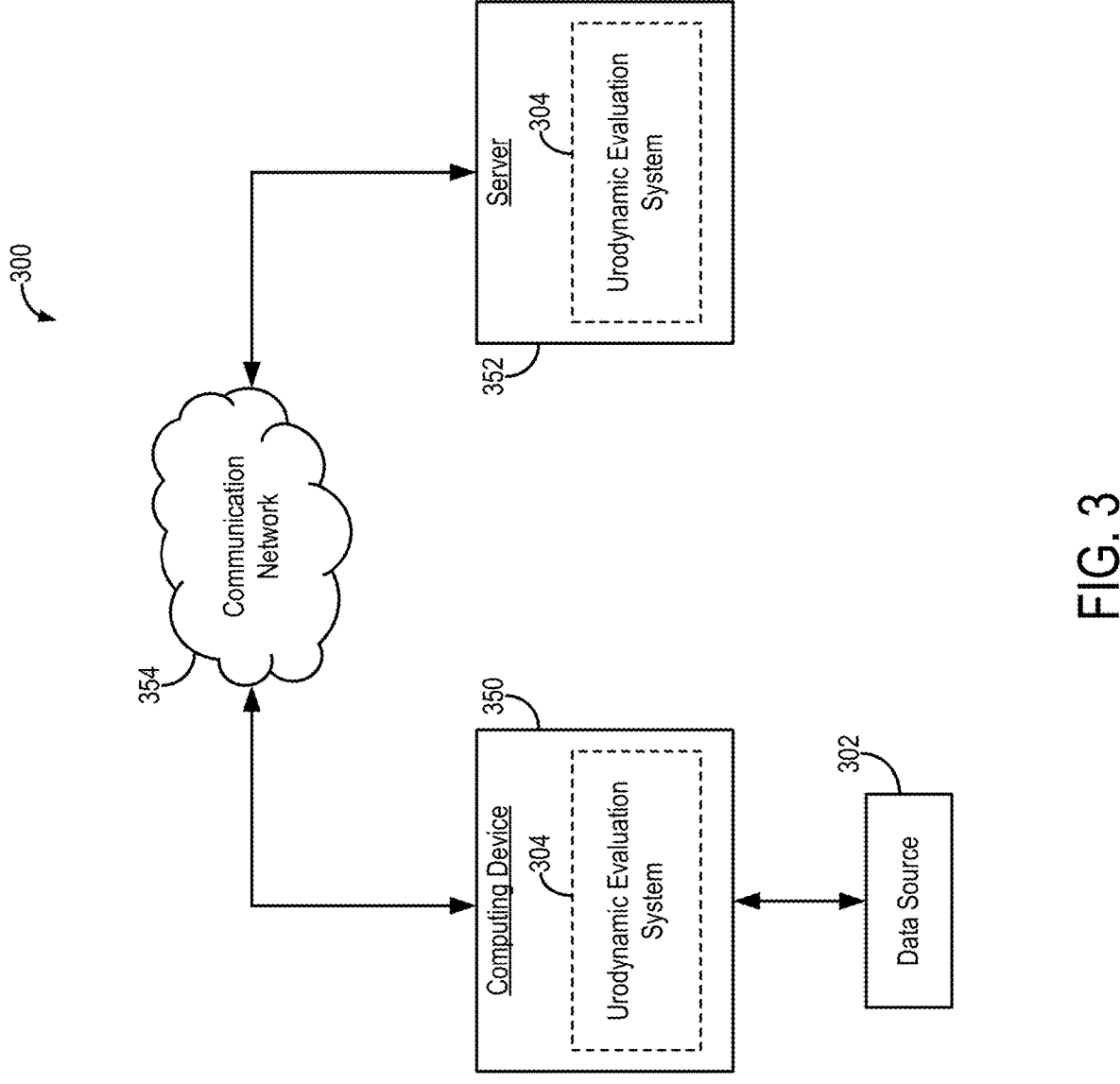
FIG. 3 is a block diagram of an example urodynamic evaluation system.

Referring now to FIG. 3, an example of a system 300 for urodynamic evaluation from ultrasound data in accordance with some embodiments of the systems and methods described in the present disclosure is shown. As shown in FIG. 3, a computing device 350 can receive one or more types of data (e.g., 2D US data, 3D US data, cine US data, uroflowmetry data) from data source 302, which may be an ultrasound system and/or uroflowmetry system. In some embodiments, computing device 350 can execute at least a portion of a urodynamic evaluation system 304 to generate a CFD model from ultrasound data received from the ultrasound data source 302 and/or uroflowmetry system.

Additionally or alternatively, in some embodiments, the computing device 350 can communicate information about data received from the data source 302 to a server 352 over a communication network 354, which can execute at least a portion of the urodynamic evaluation system 304. In such embodiments, the server 352 can return information to the computing device 350 (and/or any other suitable computing device) indicative of an output of the urodynamic evaluation system 304.

In some embodiments, computing device 350 and/or server 352 can be any suitable computing device or combination of devices, such as a desktop computer, a laptop computer, a smartphone, a tablet computer, a wearable computer, a server computer, a virtual machine being executed by a physical computing device, and so on. The computing device 350 and/or server 352 can also reconstruct images from the data.

In some embodiments, data source 302 can be any suitable source of image data (e.g., measurement data, images reconstructed from measurement data), such as an ultrasound system, a uroflowmetry system, another computing device (e.g., a server storing image data), and so on. In some embodiments, data source 302 can be local to computing device 350. For example, data source 302 can be incorporated with computing device 350 (e.g., computing device 350 can be configured as part of a device for capturing, scanning, and/or storing images). As another example, data source 302 can be connected to computing device 350 by a cable, a direct wireless link, and so on, Additionally or alternatively, in some embodiments, data source 302 can be located locally and/or remotely from computing device 350, and can communicate data to computing device 350 (and/or server 352) via a communication network (e.g., communication network 354).

In some embodiments, communication network 354 can be any suitable communication network or combination of communication networks. For example, communication network 354 can include a Wi-Fi network (which can include one or more wireless routers, one or more switches, etc.), a peer-to-peer network (e.g., a Bluetooth network), a cellular network (e.g., a 3G network, a 4G network, etc, complying with any suitable standard, such as CDMA, GSM, LTE. LTE Advanced, WiMAX, etc.), a wired network, and so on. In some embodiments, communication network 354 can be a local area network, a wide area network, a public network (e.g., the Internet), a private or semi-private network (e.g., a corporate or university intranet), any other suitable type of network, or any suitable combination of networks. Communications links shown in FIG. 3 can each be any suitable communications link or combination of communications links, such as wired links, fiber optic links, Wi-Fi links, Bluetooth links, cellular links, and so on.

Figure 4:
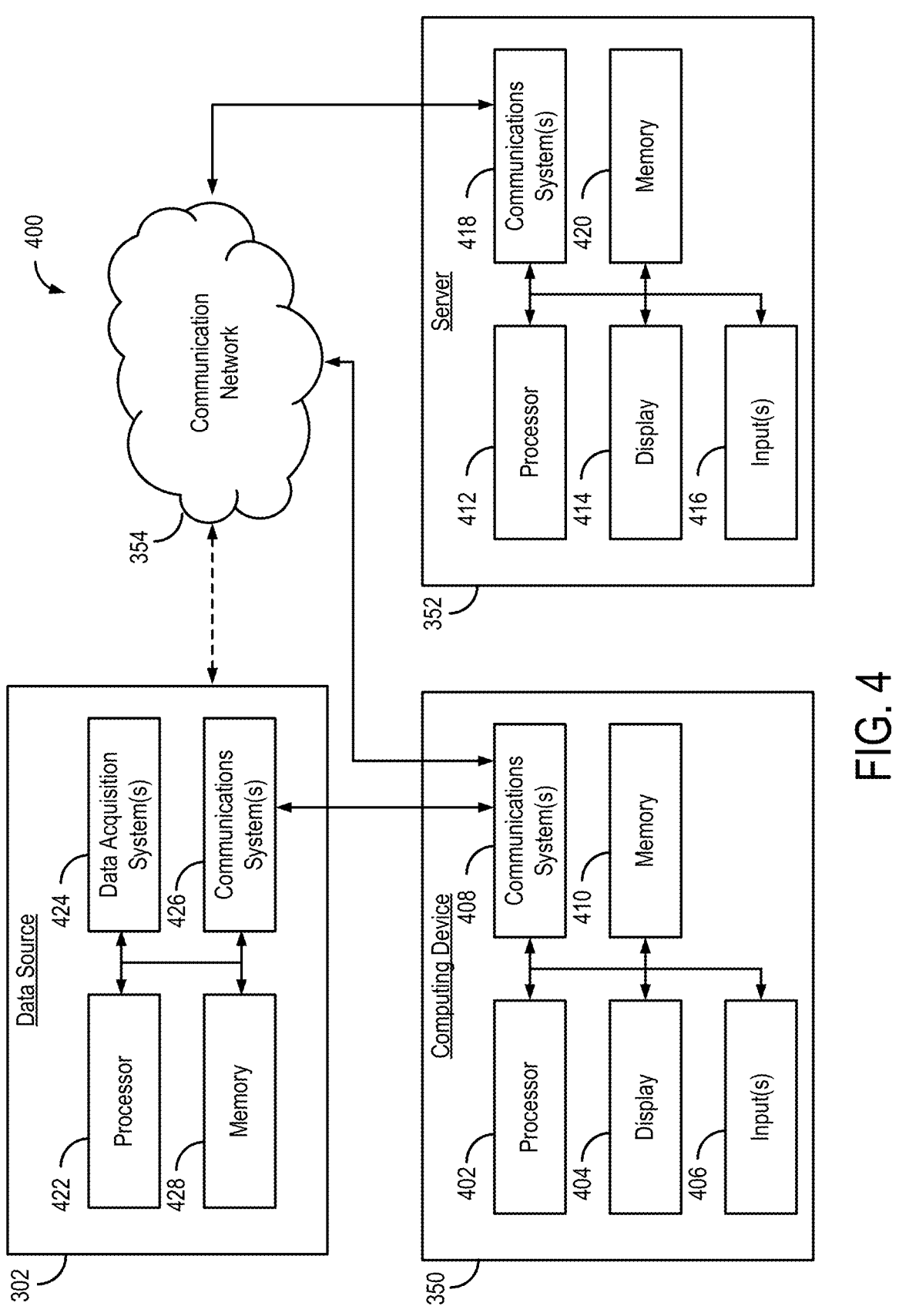
FIG. 4 is a block diagram of example components that can implement the urodynamic evaluation system of FIG. 3.

Referring now to FIG. 4, an example of hardware 400 that can be used to implement data source 302, computing device 350, and server 352 in accordance with some embodiments of the systems and methods described in the present disclosure is shown. As shown in FIG. 4, in some embodiments, computing device 350 can include a processor 402, a display 404, one or more inputs 406, one or more communication systems 408, and/or memory 410. In some embodiments, processor 402 can be any suitable hardware processor or combination of processors, such as a central processing unit ("CPU"), a graphics processing unit ("GPU"), and so on. In some embodiments, display 404 can include any suitable display devices, such as a computer monitor, a touchscreen, a television, and so on. In some embodiments, inputs 406 can include any suitable input devices and/or sensors that can be used to receive user input, such as a keyboard, a mouse, a touchscreen, a microphone, and so on.

In some embodiments, communications systems 408 can include any suitable hardware, firmware, and/or software for communicating information over communication network 354 and/or any other suitable communication networks. For example, communications systems 408 can include one or more transceivers, one or more communication chips and/or chip sets, and so on. In a more particular example, communications systems 408 can include hardware, firmware and/or software that can be used to establish a Wi-Fi connection, a Bluetooth connection, a cellular connection, an Ethernet connection, and so on.

In some embodiments, memory 410 can include any suitable storage device or devices that can be used to store instructions, values, data, or the like, that can be used, for example, by processor 402 to present content using display 404, to communicate with server 352 via communications system(s) 408, and so on Memory 410 can include any suitable volatile memory, non-volatile memory, storage, or any suitable combination thereof. For example, memory 410 can include RAM, ROM, EEPROM, one or more flash drives, one or more hard disks, one or more solid state drives, one or more optical drives, and so on. In some embodiments, memory 410 can have encoded thereon, or otherwise stored therein, a computer program for controlling operation of computing device 350. In such embodiments, processor 402 can execute at least a portion of the computer program to present content (e.g., images, user interfaces, graphics, tables), receive content from server 352, transmit information to server 352, and so on.

In some embodiments, server 352 can include a processor 412, a display 414, one or more inputs 416, one or more communications systems 418, and/or memory 420. In some embodiments, processor 412 can be any suitable hardware processor or combination of processors, such as a CPU, a GPU, and so on. In some embodiments, display 414 can include any suitable display devices, such as a computer monitor, a touchscreen, a television, and so on. In some embodiments, inputs 416 can include any suitable input devices and/or sensors that can be used to receive user input, such as a keyboard, a mouse, a touchscreen, a microphone, and so on.

In some embodiments, communications systems 418 can include any suitable hardware, firmware, and/or software for communicating information over communication network 354 and/or any other suitable communication networks. For example, communications systems 418 can include one or more transceivers, one or more communication chips and/or chip sets, and so on. In a more particular example, communications systems 418 can include hardware, firmware and/or software that can be used to establish a connection, a Bluetooth connection, a cellular connection, an Ethernet connection, and so on.

In some embodiments, memory 420 can include any suitable storage device or devices that can be used to store instructions, values, data, or the like, that can be used, for example, by processor 412 to present content using display 414, to communicate with one or more computing devices 350, and so on. Memory 420 can include any suitable volatile memory, non-volatile memory, storage, or any suitable combination thereof. For example, memory 420 can include RAM, ROM, EEPROM, one or more flash drives, one or more hard disks, one or more solid state drives, one or more optical drives, and so on. In some embodiments, memory 420 can have encoded thereon a server program for controlling operation of server 352. In such embodiments, processor 412 can execute at least a portion of the server program to transmit information and/or content (e.g., data, images, a user interface) to one or more computing devices 350, receive information and/or content from one or more computing devices 350, receive instructions from one or more devices (e.g., a personal computer, a laptop computer, a tablet computer, a smartphone), and so on.

In some embodiments, data source 302 can include a processor 422, one or more data acquisition system(s) 424, such as one or more ultrasound transducer and/or a uroflowmetry system 424, one or more e communications systems 426, and/or memory 428. In some embodiments, processor 422 can be any suitable hardware processor or combination of processors, such as a CPU, a GPU, and so on. In some embodiments, the one or more ultrasound transducers of the data acquisition system(s) 424 are generally configured to acquire data, images, or both. Additionally or alternatively, in some embodiments, one or more ultrasound transducers of the data acquisition system(s) 424 can include any suitable hardware, firmware, and/or software for coupling to and/or controlling operations of the ultrasound transducers. In some embodiments, one or more portions of the ultrasound transducer(s) of the data acquisition system(s) 424 can be removable and/or replaceable.

Note that, although not shown, data source 302 can include any suitable inputs and/or outputs. For example, data source 302 can include input devices and/or sensors that can be used to receive user input, such as a keyboard, a mouse, a touchscreen, a microphone, a trackpad, a trackball, and so on. As another example, data source 302 can include any suitable display devices, such as a computer monitor, a touchscreen, a television, etc., one or more speakers, and so on.

In some embodiments, communications systems 426 can include any suitable hardware, firmware, and/or software for communicating information to computing device 350 (and, in some embodiments, over communication network 354 and/or any other suitable communication networks). For example, communications systems 426 can include one or more transceivers, one or more communication chips and/or chip sets, and so on. In a more particular example, communications systems 426 can include hardware, firmware and/or or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 428 can include any suitable storage device or devices that can be used to store instructions, values, data, or the like, that can be used, for example, by processor 422 to control the one or more data acquisition system(s) 424, and/or receive data from the one or more data acquisition system(s) 424; to images from data; present content (e.g., images, a user interface) using a display, communicate with one or more computing devices 350; and so on. Memory 428 can include any suitable volatile memory, non-volatile memory, storage, or any suitable combination thereof. For example, memory 428 can include RAM, ROM, EEPROM, one or more flash drives, one or more hard disks, one or more solid state drives, one or more optical drives, and so on. In some embodiments, memory 428 can have encoded thereon, or otherwise stored therein, a program for controlling operation of data source 302. In such embodiments, processor 422 can execute at least a portion of the program to generate images, transmit information and/or content (e.g., data, images) to one or more computing devices 350, receive information and/or content from one or more computing devices 350, receive instructions from one or more devices (e.g., a personal computer, a laptop computer, a tablet computer, a smartphone, etc.), and so on.

Figure 5:
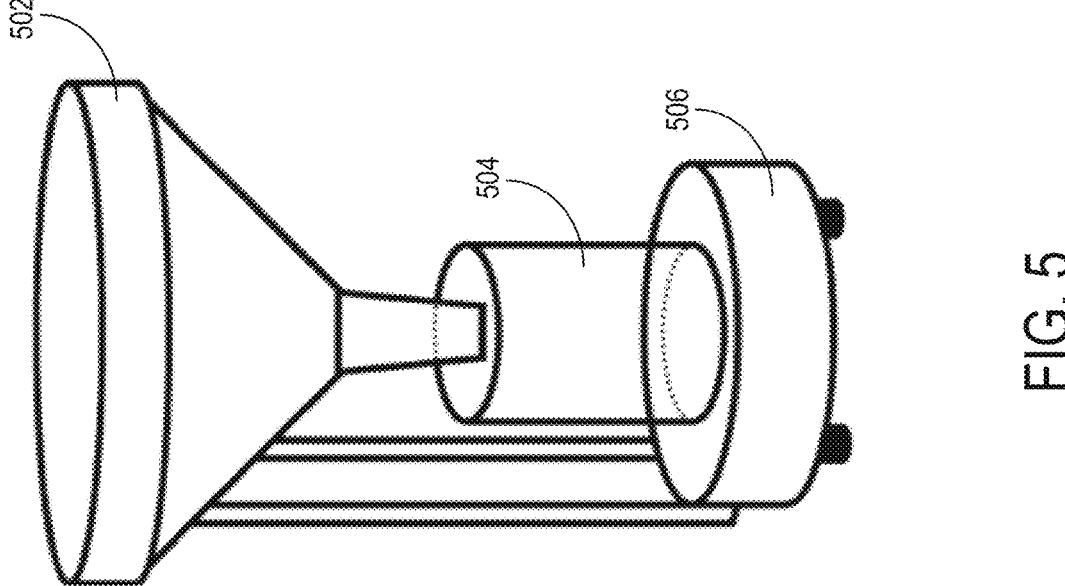
FIG. 5 is a diagram of an example uroflowmetry system, according to aspects of the present disclosure.

FIG. 5 shows an example data acquisition system 424 as a weight-based load cell uroflowmetry system 500 used in conventional uroflowmetry assessments. The uroflowmetry system 500 includes a funnel 502 for collecting and directing urine from a patient into a container 504. The container 504 sits on top of a load cell 506 that is configured to sense the variation in weight over time during urination.

Referring back to FIG. 1B, at steps 110-116, the segmented images extending over the dynamic process are processed to map a surface of the bladder. In particular, referring to FIGS. 6A-6C, one non-limiting example of a process for producing surface files is illustrated. The surface files, together, can be formed into a sequence of surface files that represent the surface of the bladder wall at each time phase during the voiding event. These surfaces are formed by different number of triangular elements and of different topologies. To allow for processing across the time-series of images acquired from across the whole dynamic process (e.g., rather than just a point prior to voiding and a point after voiding), the surfaces are converted into surfaces that are consistent across the time-series of images. For example, in one, non-limiting implementation, consistency between images may be achieved by using the same number of triangular elements (or other shapes) and same topology between adjacent images or volumes, while preserving the shape of the bladder wall within a given image frame.

In accordance with one example in accordance with the present disclosure, these 3D objects can be formed of discrete triangular elements that evolve over the entire dynamic process.

Referring to FIG. 6A, a given phase 600 of the bladder is selected for surface mapping to serve as a base surface that is the reference surface onto which all other surfaces are mapped onto. In one non-limiting example, the surface at the middle of the voiding sequence may be chosen to be the base surface, as opposed to a surface at the beginning or prior to voiding or at the end of voiding. The selected base surface is translated about a vector $(\vec{z}_i)$ such that the center of the bladder is at the origin. All the surfaces can be translated by the same vector to preserve the bladder's relative position during voiding.

Adjacent image volumes are processed. The selected surface at the given phase 600 is selected to act as a base surface (surface0), which defines the adjacent surface as surface1 from an adjacent phase 602. First, the coordinates of the vertices of the triangle elements of surface0 and surface1 are transformed from cartesian to cylindrical coordinate system. In one nonlimiting example, the axial direction of the cylindrical coordinate system can be chosen as a vector from the bladder neck to the top of the bladder dome $(\vec{z}_i)$, such that translation is about $q_i$, as illustrated in FIG. 6A.

In particular, in the given phase 600, the axial vector for surface0 is $\vec{z}_0$ and, in the adjacent phase, the axial vector for surface1 is $\vec{z}_1$. In the adjacent phase 602, the surface can be petitioned in longitudinal and angular directions. A vector can be defined such that $\vec{n} = \vec{z}_0 \times \vec{z}_1$ and an angle can be defined such that angle $\alpha = \text{across} (\vec{z}_0 \cdot \vec{z}_1)$. Therefore, two cylindrical coordinate systems are defined, one for each surface. A transformation matrix, A, can be used to transform the coordinates system for surface0 to that of surface1, for example, where the matrix is given by:

$$A = \begin{bmatrix} \cos(\alpha) + n_1^2(1 - \cos(\alpha)) & n_1 n_2(1 - \cos(\alpha)) - n_3\sin(\alpha) & n_1 n_3(1 - \cos(\alpha)) + n_2\sin(\alpha) \\ n_1 n_2(1 - \cos(\alpha)) + n_3\sin(\alpha) & \cos(\alpha) + n_2^2(1 - \cos(\alpha)) & n_2 n_3(1 - \cos(\alpha)) - n_1\sin(\alpha) \\ n_1 n_3(1 - \cos(\alpha)) - n_2\sin(\alpha) & n_2 n_3(1 - \cos(\alpha)) + n_1\sin(\alpha) & \cos(\alpha) + n_3^2(1 - \cos(\alpha)) \end{bmatrix}$$

where $\vec{n} = \begin{bmatrix} n_1 \\ n_2 \\ n_3 \end{bmatrix}$.

With common coordinate systems, the surfaces can be binned. Referring to FIG. 6B, in this non-limiting example, surface1 can be divided into sections in the axial and azimuthal directions. In this example, surface1 of the adjacent phase 602 can be divided into, for example, 12-20 sections. In each section, the radial distance required to intersect each triangle element can be found in surface1 to the closest triangle in surface0. This can be achieved by solving a system of equations with the previously calculated transformation matrix, A. After solving for every triangle element, this process can be repeated for other sections. Binning reduces the computational demand by reducing the number triangles when searching for surface0's closest triangle. In this way, though optional, binning reduces the number of operations and runtime for the mapping algorithm.

These radial distances can be used to generate a new surface file. This is the mapped version of surface1, which can be referred to as surface1r 604, which is illustrated in FIG. 6C. Surface1r has the same number of triangle elements and topology as surface0. This process is then repeated between surface1r and surface2, where surface2 is the bladder wall surface from the successive cine scan time points. These processes can be repeated for every surface or a select number of surfaces, to create mapped surfaces. Every mapped surface has the same number of triangle elements and topology, but the shapes are the same as the bladder wall at their corresponding time phase.

As previously described, the process described herein can map surfaces to a flow model. In one non-limiting example, the mapped surfaces are provided to a computational flow dynamics (CFD) model. In one particular, non-limiting example, the mapped surfaces can be loaded into a CFD model using CONVERGE, available from Convergent Science, Inc., Madison, Wisconsin, USA, along with the time-stamp for each surface. Regardless of the particular implementation, the CFD model may provide a wall motion driven CFD simulation, where the outlet is the bladder neck and the pressure can be controlled relative to the bladder neck. This general CFD model can be coupled with a CFD model of the urethra to impose the bladder neck pressure. In one further, non-limiting example, a pressure-implicit with splitting of operators (PISO) algorithm can be used as a Navier-Stokes equation solver. The dimensions of the cubic mesh elements can be controlled.

By using ultrasound data acquired over the full dynamic process, the CFD models are designed to provide comprehensive information on the dynamics of, for example, bladder voiding comparable to clinically available methods of multi-channel urodynamic studies that require direct and invasive measures of urodynamics. That is, a report can be clinically consistent with those generated by invasive, multi-channel urodynamic studies.

Figure 7A:
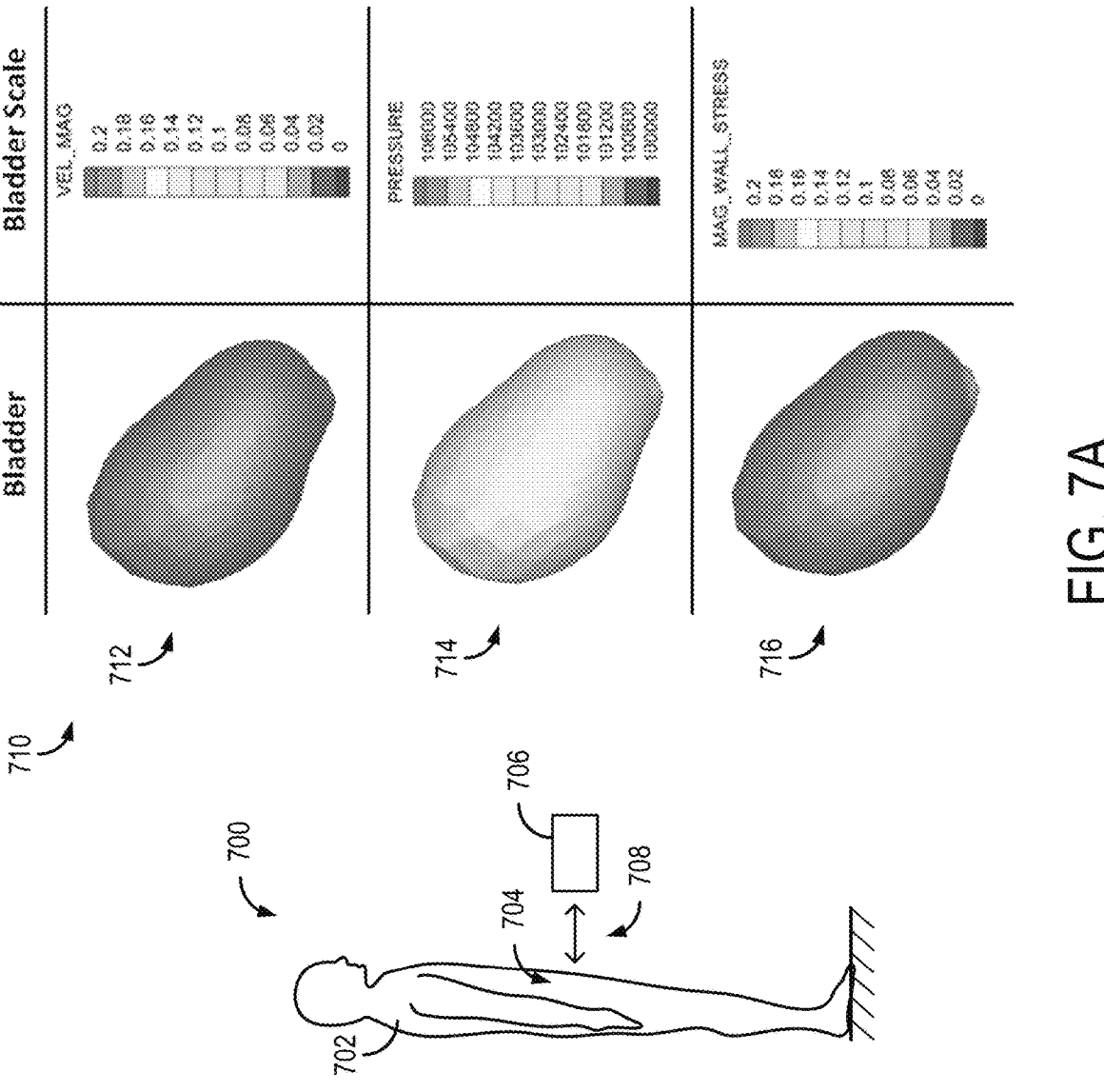
FIG. 7A is a non-limiting example of visualizations, that can be included in a report generated in accordance with the present disclosure.

FIG. 7A shows an example suite of information that may be included in a report. The report may be generated from a subject 702 in a seated or upright position 700. This may facilitate a natural bladder voiding position. Alternatively, the subject 702 may be in a supine position. The anatomy 704, for example the bladder, of the subject 702 is imaged using an ultrasound system 706, wherein ultrasound signal is transmitted and reflected back 708 from bladder 704. In a non-limiting example, the ultrasound system 706 may be the system previously described in FIGS. 3-5.

The information 710 includes images or movies of the anatomy 704, and/or images or movies of the whole anatomy or portions of the anatomy with particular metrics illustrated in visualizations, such as coloration of 3D images or movies. In the non-limiting example illustrated in FIG. 7A, the bladder is isolated and illustrated over time with colorizations to show velocity 712, pressure 714, and wall shear stress 716.

Beyond movies and/or metrics registered to anatomical data, the metrics can be reported over time, such as illustrated in FIG. 7B. Again, because the above-described systems and methods facilitate the use of ultrasound data or uroflowmetry data acquired over the entire bladder voiding, any metric can be reported over time. For example, as illustrated in FIG. 7B, flow rate can be reported over time 718. As such, the actual maximum flow rate can be determined, not just estimated from interpolated data. Furthermore, the actual time of the maximum flow rate can be determined, not estimated. Such metrics can be reported for the entire system or separated into particular anatomy, such as bladder versus urethra, which is not possible with interpolated data or even using multichannel studies. For example, the pressure drop can be shown over time 720 for penile, membranous, and prostatic data.

Irrespective of the particular information or way of presenting information within a given report, the systems and methods provided herein are able to provide the clinical information currently only available to clinicians via multichannel urodynamic studies. However, the systems and methods described herein are non-invasive and, for the first time, provides detailed anatomic and functional information on the lower urinary tract during the entire voiding cycle. A variety of additional information not previously available to clinicians facilitates a deeper understanding of impaired contractility by identifying and characterizing specific putative causes such as global hypokinesis, dyscoordination of bladder contraction, or loss of bladder power due to intravesical flow vortices.

Thus, the systems and methods provided herein comprehensively characterize the bladder and lower urinary tract biomechanics by using ultrasound based computational fluid dynamics. No changes to the scanner hardware or acquisition algorithms are required. The ultrasound data may be processed locally or sent to a remote location to perform segmentation, analysis, and reporting. In any case, a report is generated for the clinician that provides direct measures typically only available via multichannel urodynamic studies, but also provides substantial information that can better inform clinical decisions.

Additionally, while the above-described systems and methods focused on "voiding," the systems and methods also readily apply to bladder filling. That is, some studies suggest that bladder filling is an active process (not just passive filling but actual bladder muscle accommodation and possible micro-motions). In addition, many patients with LUTS experience so-called "involuntary bladder contractions that produce symptoms or urinary urgency and/or urge incontinence. Similarly, some women experience so-called stress incontinence that is precipitated by a Valsalva maneuver, such as coughing or straining. These and other dynamics can readily be studied, imaged, and/or included in reports using the above-described systems and methods.

The invention has been described according to one or more preferred embodiments, and it should be appreciated that many equivalents, alternatives, variations, and modifications, aside from those expressly stated, are possible and within the scope of the invention.

The preceding discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown but are to be accorded the widest scope consistent with the principles and features disclosed herein. The detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

It is to be understood that the disclosure is not limited in its application to the details of construction and the arrangement of components set forth in the description or illustrated in the drawings. The disclosure is capable of other embodiments and of being practiced or of being carried out in various ways. Also, it is to be understood that the phraseology and terminology used herein is for the purpose of description and should not be regarded as limiting.

The invention claimed is:

1. A method for urodynamic evaluation during voiding of a bladder, the method comprising:
   receiving an ultrasound cine scan of a voiding event of a bladder of a subject, wherein the ultrasound cine scan includes images of a first bladder volume before the voiding event, of a second bladder volume after the voiding event, and of the voiding event between the first bladder volume and second bladder volume;
   segmenting the images of the first bladder volume and the image of the second bladder volume to determine the first bladder volume and the second bladder volume;
   generating a three-dimensional (3D) virtual model of the bladder from each of the first bladder volume and the second bladder volume;
   deriving flow information during the voiding event;
   generating a flow curve from the flow information;
   inputting the 3D virtual model and the flow curve into a computational fluid dynamics (CFD) model; and
   generating a report using the inputs of the CFD model.

2. The method of claim 1, wherein the first bladder volume is greater than the second bladder volume.

3. The method of claim 2, wherein the first bladder volume is at a maximum bladder volume and the second bladder volume is at a minimum bladder volume.

4. The method of claim 1, wherein the 3D virtual model is registered to a spherical coordinate system.

5. The method of claim 1, wherein deriving the flow information during the voiding event includes segmenting the images to determine a deformation of the bladder.

6. The method of claim 5, further comprising defining a series of structural elements across a segmented bladder in the images of the first bladder volume, the second bladder volume, and during the voiding event.

7. The method of claim 6, wherein the structural elements are triangles and further comprising enforcing a consistent number of triangles across the image of the first bladder volume, the second bladder volume, and the voiding event, while preserving a shape of the bladder.

8. The method of claim 7, further comprising determining at least one of bladder capacity, voiding pressure, flow dynamics, pressure at maximum flow, post voiding residual volume, emptying efficiency, or maximum flow to determine one or more metrics describing function of a urinary tract during voiding.

9. The method of claim 8, comprising producing at least one of the images with functional overlays, graphs showing the one or more metrics over time, or metric-correlated indices including at least one of bladder outlet obstruction index (BOOI) or bladder contractility index (BCI).

10. The method of claim 1, further comprising receiving a uroflowmetry acquisition during the voiding event.

11. The method of claim 10, wherein the uroflowmetry acquisition generates an output including at least one of a urine voiding volume, a urine voiding speed, and a total urine voiding time.

12. The method of claim 11, wherein the CFD model receives the output.

13. The method of claim 1, wherein the ultrasound cine scan is performed while the subject is in an upright or seated position.

14. An ultrasound imaging system comprising:
   a transducer configured to transmit an ultrasound signal to a region of interest including a bladder of a subject during a voiding event and receive a reflected ultrasound signal from the region of interest;
   a processor coupled to the transducer and configured to:
   receive the reflected ultrasound signal;
   generate a plurality of images from the received signal of the region of interest during the voiding event;
   segment a first image of the region of interest to determine a first bladder volume and a second image of the region of interest to determine a second bladder volume;
   generate a three-dimensional (3D) virtual model of the bladder from each of the first bladder volume and the second bladder volume;
   derive flow information during the voiding event;
   generate a flow curve from the flow information;
   input the 3D virtual model and the flow curve into a computational fluid dynamics (CFD) model; and
   generate a report using the inputs of the CFD model.

15. The system of claim 14, wherein the first bladder volume is greater than the second bladder volume.

16. The system of claim 15, wherein the first bladder volume is at a maximum bladder volume and the second bladder volume is at a minimum.

17. The system of claim 14, wherein the 3D virtual model is registered to a spherical coordinate system.

18. The system of claim 14, wherein deriving the flow information during the voiding event includes segmenting the plurality of images to determine a deformation of the bladder.

19. The system of claim 18, wherein the processor is further configured to define a series of structural elements across a segmented bladder in each of the images of the first bladder volume, the second bladder volume, and the voiding event.

20. The system of claim 19, wherein the structural elements are triangles, and the processor is further configured to enforce a consistent number of triangles across the image of the first bladder volume, the image of the second bladder volume, and the plurality of images during the voiding event, while preserving a shape of the bladder.

21. The system of claim 20, wherein the processor is further configured to determine at least one of bladder capacity, voiding pressure, flow dynamics, pressure at maximum flow, post voiding residual volume, emptying efficiency, or maximum flow to determine one or more metrics describing function of a urinary tract during voiding.

22. The system of claim 21, wherein the processor is further configured to produce at least one of images with functional overlays, graphs showing the one or more metrics over time, or metric-correlated indices including at least one of bladder outlet obstruction index (BOOI) or bladder contractility index (BCI).

23. The system of claim 14, wherein the processor is further configured to receive uroflowmetry acquisition during the voiding event.

24. The system of claim 23, wherein the uroflowmetry acquisition generates an output including at least one of a urine voiding volume, a urine voiding speed, and a total urine voiding time.

25. The system of claim 24, wherein the CFD model receives the output.

26. The system of claim 14, wherein the ultrasound signal is transmitted and received from the region of interest while the subject is in an upright or seated position.

\* \* \* \* \*